United States Patent
Edwards et al.

[11] Patent Number: 5,822,032
[45] Date of Patent: Oct. 13, 1998

[54] INTERPUPILLARY DISTANCE MEASURING DEVICE

[75] Inventors: John L. Edwards, Sarasota; Michael D. Franz, Siesta Key; Todd C. Perkins, Bradenton, all of Fla.

[73] Assignee: Morrison International, Sarasota, Fla.

[21] Appl. No.: 896,880

[22] Filed: Jul. 18, 1997

[51] Int. Cl.⁶ .................................................. G02C 3/10
[52] U.S. Cl. ............................................................ 351/204
[58] Field of Search ............................................. 351/204

[56] References Cited

U.S. PATENT DOCUMENTS

| | | | |
|---|---|---|---|
| 3,115,713 | 12/1963 | Johnston | 351/204 |
| 3,451,747 | 6/1969 | Kirchhubel | 351/204 |
| 3,752,566 | 8/1973 | Mathews | 351/204 |
| 4,131,338 | 12/1978 | Zaleeski | 351/204 |
| 4,244,639 | 1/1981 | Kanda | 351/204 |
| 4,944,585 | 7/1990 | Mizuno | 351/204 |
| 5,461,434 | 10/1995 | Blattberg | 351/204 |

*Primary Examiner*—Huy Mai
*Attorney, Agent, or Firm*—K. Lukacher; M. Lukacher

[57] ABSTRACT

An improved device for measuring the interpupillary distance of the eyes of a person is provided. The device has a frame having a first hole which is positionable at the pupil of the person's left eye, and a disk mounted juxtaposed to the frame which is rotatable about an axis perpendicular to the face of the frame. The disk has a plurality of second holes, extending through the disk from its surface, which spiral radially outward on said disk from the axis. By rotating the disk, one of the second holes is viewable through a window in the frame and positionable at the pupil of the person's right eye. The interpupillary distance is equal or approximately equal to the distance between the centers of the first and second holes when the holes are positioned at the respective pupils of the person. Numerals representing this distance appear on the surface of the disk through another window in the frame.

19 Claims, 1 Drawing Sheet

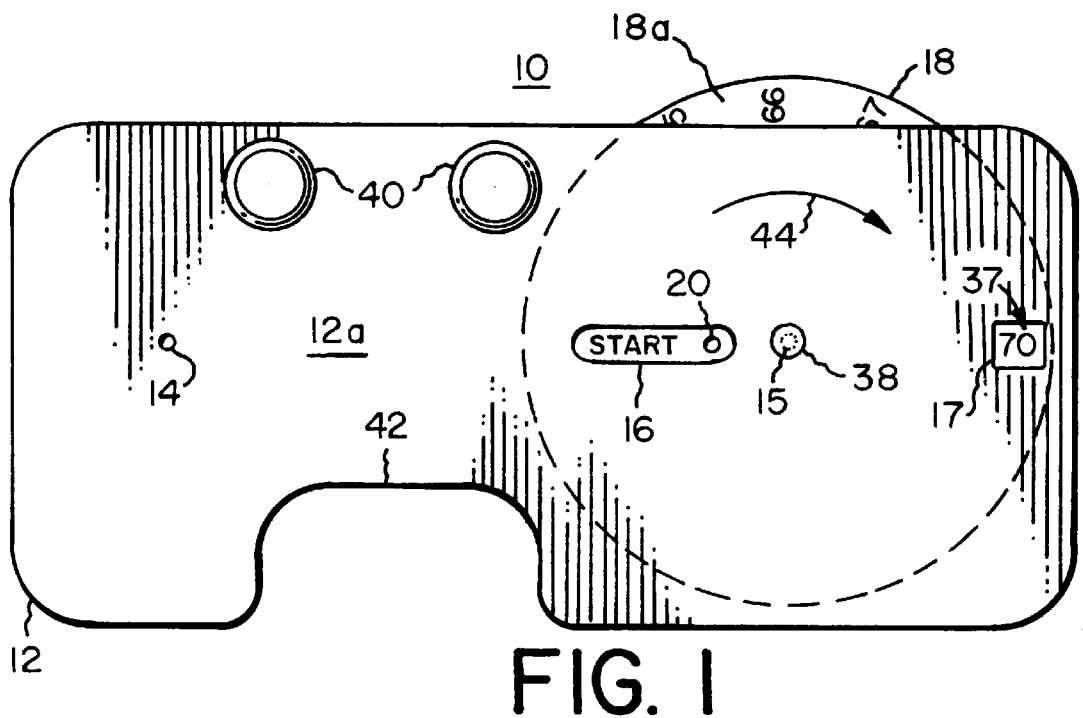
FIG. 1
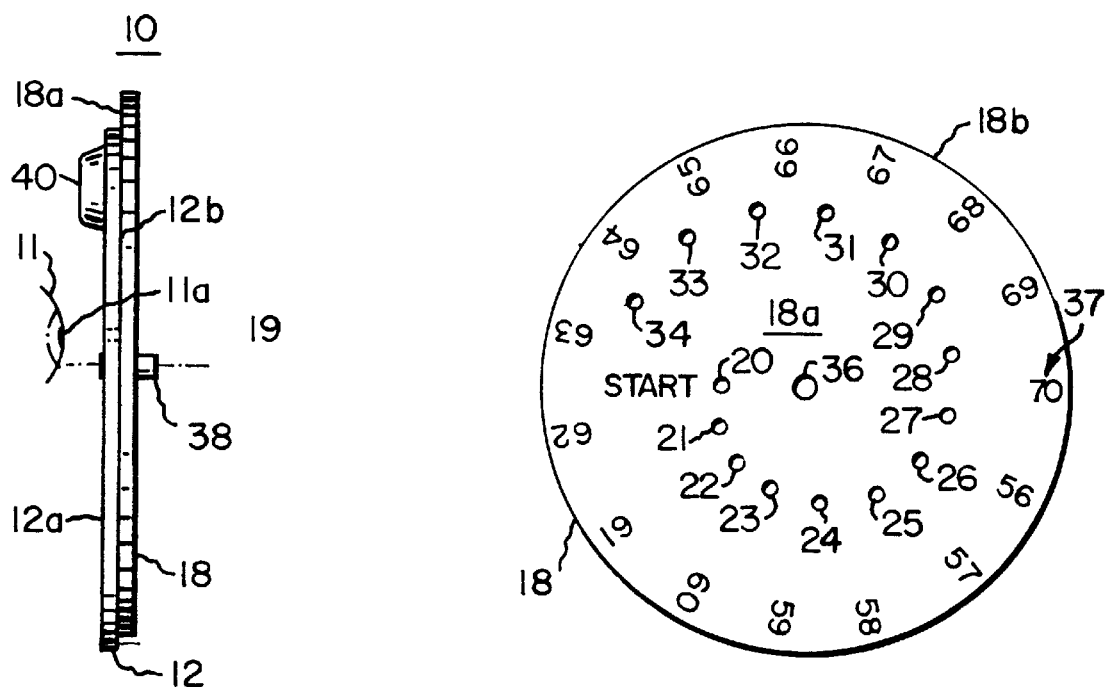
FIG. 2
FIG. 3

INTERPUPILLARY DISTANCE MEASURING DEVICE

FIELD OF THE INVENTION

The present invention relates to a device (and method) for measuring interpupillary distance, and relates particularly to, a device which allows a person to easily measure their own interpupillary distance without the assistance of another person.

BACKGROUND OF THE INVENTION

An important measurement in the dispensing of eyeglass (or spectacle) frames is interpupillary distance (IPD), i.e., the distance between a person's pupils. IPD is generally used for setting the optical centers of lenses in the eyeglass frames to provide a person with proper vision correction.

Several devices have been proposed for measuring interpupillary distance. Some require complex optical arrangements and are quite costly to manufacture, as shown for example in U.S. Pat. No. 4,944,585 to Mizuno, issued Jul. 31, 1990. Other devices for measuring interpupillary distance require operation by an optometrist or other eye care professional. In this regard, U.S. Pat. No. 4,131,338 to Zalewski, issued Dec. 26, 1978, describes a spectacle frame worn by an optometrist for measuring interpupillary distance; and U.S. Pat. No. 3,752,566 to Mathews, issued Aug. 14, 1973, shows a scaled elongated rule used by an eye care practitioner to measure interpupillary distance.

Often in dispensing eyeglass frames it would be useful if the person who will be wearing the frames could measure their own IPD. This may avoid the need for the person to visit an optometrist or other eye care professional to measure their IPD. One proposed apparatus which may allow a person to measure their IPD is described in U.S. Pat. No. 5,461,434 to Blattberg, issued Oct. 24, 1995. Blattberg describes a device having a pair of sliders which move horizontally in a frame, and adhesive elements for fixing the position of the sliders. The sliders each have a viewing hole and are moved such that the person properly sees through the viewing holes. No mechanism is provided in Blattberg for allowing a person to read on the device their IPD. One drawback of this device is that it is complex to manufacture since it requires three parts, two of which must be movable. Another drawback is that a separate scaled ruler may be needed to measure the distance between viewing holes to obtain the person's IPD.

SUMMARY OF THE INVENTION

A principal object of the present invention is to provide an improved device (and method) for measuring IPD which can allow a person to easily and accurately measure their own IPD without the assistance of another person.

Another object of the present invention is to provide an improved device for measuring IPD which is not complex and can be manufactured at a low cost.

A further object of the present invention is to provide an improved device for measuring IPD by which the person using the device can read their IPD directly from the device.

Briefly described, a device embodying the invention can be operated by a person, without assistance, for measuring the interpupillary distance between the pupils of the eyes of that person. The device includes a frame having a face and a first hole extending through the frame from the face which is positionable at one of the person's two pupils. A disk is mounted juxtaposed to the frame which is rotatable about an axis perpendicular to the frame's face. The disk has a surface and a plurality of second holes extending through the disk from its surface. By rotating the disk, one of the second holes is positionable at the other of the person's pupils. The interpupillary distance (IPD) is equal or approximately equal to the distance between the centers of the first and second holes when the holes are positioned at the person's respective pupils.

As the disk is rotated, the second holes are separately viewable through a window in the frame. Another window is also provided in the frame through which appear indicia, such as numerals, on the surface of the disk which represent the distance between the centers of the first and second holes when positioned at the person's respective pupils.

To measure IPD with the above device, a person views through the first hole with one eye and rotates the disk until the person sees a single field of view when viewing with the other eye through one of the second holes. On the surface of the disk, indicia are displayed to the person representing a distance equal or approximately equal to the person's IPD.

BRIEF DESCRIPTION OF THE DRAWINGS

The foregoing objects, features and advantages of the invention will become more apparent from a reading of the following description in connection with the accompanied drawings, in which:

FIG. 1 is a plan-view of a device for measuring IPD in accordance with the present invention;

FIG. 2 is a side-view of the device of FIG. 1; and

FIG. 3 is a plan-view of the disk in the device of FIGS. 1 and 2.

DETAILED DESCRIPTION OF THE INVENTION

Referring to FIGS. 1 and 2, a device 10 is shown for measuring interpupillary distance (IPD). Device 10 has a frame 12 composed of a substantially rigid material, such as plastic. Frame 12 has a face 12a and a hole 14 extending through frame 12 from face 12a to an opposing surface 12b of frame 12. Device 10 also has a disk 18 mounted juxtaposed to surface 12b of frame 12 which is rotatable about an axis 19 perpendicular to face 12a and surface 12b. To mount disk 18 to frame 12, a coupler 38 couples disk 18 to frame 12 and provides sufficient friction such that disk 18 does not freely rotate, but is rotatable. Coupler 38 may be a pin which passes through a hole 15 (shown in dotted lines in FIG. 1) in frame 12 and a hole 36 (FIG. 3) in disk 18 centered on axis 19.

As shown in FIG. 3, disk 18 has a surface 18a and a plurality of holes 20–34 extending through disk 18 from surface 18a. Holes 20–34 are positioned on disk 18 along a spiral which extends radially outward from axis 19 over a portion of disk 18. Preferably, holes 14 and 20–34 are each approximately 1.5 mm in diameter. When disk 18 is mounted to frame 12, surface 18a of disk 18 is adjacent to surface 12b of frame 12. Disk 18 may be composed of the same substantially rigid material as frame 12.

Windows 16 and 17 are provided in frame 12 such that as disk 18 rotates about axis 19 holes 20–34 are separately viewable and positionable through window 16, and indicia 37 on surface 18a of disk 18 appears in window 17 for each of holes 20–34 at window 16. Indicia 37 may be located near outer edge 18b of disk 18.

For each of holes 20–34, indicium 37 represents a numerical distance between the center of hole 14 to the center of each of holes 20–34 when appearing though window 16. This distance may range between 70 mm for hole 20 to 56 mm for hole 34. For example, for holes 20–34, indicia 37 may respectively be 70 mm, 69 mm, 68 mm, 67 mm, 66 mm, 65 mm, 64 mm, 63 mm, 62 mm, 61 mm, 60 mm, 59 mm, 58 mm, 57 mm, and 56 mm. Other distances may also be provided based on different positions of holes at window 16. The distance represented by indicia 37 is equal to the IPD of a person, the distance between the pupils of their eyes, when hole 14 is positioned at the pupil of one eye of the person (such as the left eye) and one of holes 20–34 is positioned at the pupil of the other eye of the person (such as the right eye). The distance represented by indicia 37 may approximately be equal to the IPD of a person using device 10 if holes 14 and/or one of holes 20–34 when positioned at the person's respective pupils do not exactly align with the pupils. Eye 11 with pupil 11a is illustrated in FIG. 2 to represent either of the person's eyes when viewing through hole 14 or one of holes 20–34 at window 16. Although indicia 37 is described herein as numerals, other types of indicia or symbols may be used to represent IPD, such as letters. Also on surface 18a of disk 18 may be wording, such as "START", when hole 20 is positioned at window 16.

Frame 12 further has a notch 42 for supporting frame 12 on the nose of the person using device 10. A pair of buttons 40 fixed on surface 12a of the frame 12 is provided for supporting frame 12 on the forehead of the person when using device 10. Buttons 12 may be made of a silicon-based material, polyurethane, or other similar material.

To operate device 10, a person rotates disk 18 until "START" appears in window 16 if "START" is not already present. The person while not wearing eyeglasses, holds device 10 such that frame 12 is supported in a level position on the person's nose at notch 42 and buttons 40 lie against the person's forehead. The person then positions frame 12 such that the left eye of the person views through hole 14. This positions the left pupil of the person approximately at the center of hole 14. The person then rotates disk 18 in the direction of arrow 44 until the person views with their right eye through one of holes 20–34 a single visual field, similar to that of binoculars. A target may be positioned in front of the person to assist is establishing a visual reference in the visual field. After a single visual field is established, the person stops rotating disk 18 and reads their IPD measurement (indicia 37) through window 17. This measurement is equal or approximately equal to the person's IPD depending on how close their pupils aligned on holes 14 and the selected one of holes 20–34 providing a single visual field.

In addition to device 10 being used by a person to measure their IPD for fitting eyeglass frames, the device could also be used by another, such as an optometrist, to measure a person's IPD.

From the foregoing description, it will be apparent that there has been provided an improved interpupillary distance measuring device. Variations and modifications of the herein described device in accordance with the invention will undoubtably suggest themselves to those skilled in the art. Accordingly, the foregoing description should be taken as illustrative and not in a limiting sense.

What is claimed is:

1. A device for measuring the distance between the pupils of each of the eyes of a person (IPD) comprising:
    a frame having a face and a first hole extending through said frame from said face and positionable at one of the two pupils of the person;
    a disk mounted juxtaposed to said frame which is rotatable about an axis perpendicular to said face, said disk having a surface and a plurality of second holes extending through said disk from said surface of said disk; and
    one of said plurality of second holes being positionable at the other of the pupils of said person by rotating said disk, wherein said distance is equal or approximately equal to the distance between the center of said first hole and the center of said one of said plurality of second holes.

2. The device according to claim 1 wherein said frame further comprises a window in said frame, wherein said one of said plurality of second holes is viewable through said window.

3. The device according to claim 2 wherein said frame further comprises a second window in said frame and indicia which appears on said surface of said disk through said second window, said indicia representing said distance between the center of said first hole and the center of said one of said plurality of second holes.

4. The device according to claim 1 wherein said plurality of second holes spiral radially outward on said disk from said axis over a portion of said disk.

5. The device according to claim 1 wherein said frame further comprises a surface opposite said face, and said disk is mounted to said frame juxtaposed to said surface opposite said face.

6. The device according to claim 1 further comprising means for rotatably mounting said disk to said frame.

7. The device according to claim 1 wherein said frame further comprises a notch for supporting said device on the nose of said person.

8. The device according to claim 1 wherein said frame further comprises means on said face for supporting said device on the forehead of said person.

9. The device according to claim 1 wherein each of said plurality of second holes provides for a different IPD measurement.

10. The device according to claim 1 wherein said frame and said disk are each of a substantially rigid material.

11. A method for measuring the interpupillary distance (IPD) between the pupils of each of the eyes of a person comprising the steps of:
    providing a frame having a first hole extending through said frame and positionable at one of the two pupils of the person;
    providing a disk having a plurality of second holes extending through said disk from the surface of said disk;
    rotatably coupling said disk in juxtaposition with said frame such that said disk can rotate upon an axis perpendicular to the face of said frame; and
    positioning one of said plurality of second holes at the other of said pupils of the person by rotating said disk, wherein the interpupillary distance is equal or approximately equal to the distance between the center of said first hole and the center of said one of said plurality of second holes.

12. The method according to claim 11 further comprising the step of viewing said one of said plurality of second holes through a window in said frame.

13. The method according to claim 12 further comprising the step of displaying indicia on the surface of said disk through a second window in said frame, said indicia representing the distance between the center of said first hole and the center of said one of said plurality of second holes.

14. The method according to claim 11 wherein said plurality of second holes spiral radially outward on said disk from said axis over a portion of said disk.

15. The method according to claim 11 further comprising the steps of rotatably mounting said disk to said frame.

16. The method according to claim 11 wherein said coupling step further comprises the step of mounting said disk to said frame on the surface of said frame opposite said face.

17. The method of according to claim 11 further comprising the step of providing a notch in said frame to support said frame on the nose of the person.

18. The method according to claim 11 further comprising the step of providing buttons on the face of said frame to support said frame on the forehead of the person.

19. The method according to claim 11 wherein each of said plurality of second holes provides for a different interpupillary distance.

* * * * *